(12) United States Patent
Eisinger (10) Patent No.: US 11,458,244 B2
(45) Date of Patent: Oct. 4, 2022

(54) IRRIGATING SURGICAL APPARATUS WITH POSITIVE PRESSURE FLUID

(71) Applicant: Covidien LP, Mansfield, MA (US)

(72) Inventor: Joseph Eisinger, Northford, CT (US)

(73) Assignee: COVIDIEN LP, Mansfield, MA (US)

( * ) Notice: Subject to any disclaimer, the term of this patent is extended or adjusted under 35 U.S.C. 154(b) by 0 days.

(21) Appl. No.: 17/145,765

(22) Filed: Jan. 11, 2021

(65) Prior Publication Data

US 2021/0244875 A1  Aug. 12, 2021

Related U.S. Application Data

(60) Provisional application No. 62/971,521, filed on Feb. 7, 2020.

(51) Int. Cl.
*A61B 17/064* (2006.01)
*A61M 3/02* (2006.01)
*A61B 17/115* (2006.01)

(52) U.S. Cl.
CPC ....... *A61M 3/0279* (2013.01); *A61B 17/1155* (2013.01); *A61B 2217/007* (2013.01)

(58) Field of Classification Search
CPC .................. A61B 2217/007; A61B 17/115
See application file for complete search history.

(56) References Cited

U.S. PATENT DOCUMENTS

| | | |
|---|---|---|
| 37,165 A | 12/1862 | Gary |
| 3,209,754 A | 10/1965 | Brown |
| 3,273,562 A | 9/1966 | Brown |
| 3,499,591 A | 3/1970 | Green |
| 3,528,693 A | 9/1970 | Pearson et al. |
| 3,744,495 A | 7/1973 | Johnson |
| 3,862,631 A | 1/1975 | Austin |
| 3,949,924 A | 4/1976 | Green |
| 4,060,089 A | 11/1977 | Noiles |
| 4,204,623 A | 5/1980 | Green |
| 4,217,902 A | 8/1980 | March |

(Continued)

FOREIGN PATENT DOCUMENTS

| | | |
|---|---|---|
| CN | 101683284 A | 3/2010 |
| CN | 102648864 A | 8/2012 |

(Continued)

OTHER PUBLICATIONS

Detemple, P., "Microtechnology in Modern Health Care", Med Device Technol. 9(9):18-25 (1998).

(Continued)

*Primary Examiner* — Eyamindae C Jallow
(74) *Attorney, Agent, or Firm* — Carter, DeLuca & Farrell LLP (57) ABSTRACT

A surgical instrument including an elongated tubular body portion and an irrigation assembly. The elongated tubular body portion extending distally to an end effector and defining an interior cavity. The irrigation assembly includes an inlet port and a shaft assembly supported by the elongated tubular body portion. The inlet port and the shaft assembly are disposed in fluid communication with one another to deliver fluid from the inlet port into the interior cavity of the elongated tubular body portion to irrigate the interior cavity with positive fluid pressure.

20 Claims, 7 Drawing Sheets

(56) References Cited

U.S. PATENT DOCUMENTS

| | | |
|---|---|---|
| 4,263,903 A | 4/1981 | Griggs |
| 4,275,813 A | 6/1981 | Noiles |
| 4,331,277 A | 5/1982 | Green |
| 4,428,376 A | 1/1984 | Mericle |
| 4,429,695 A | 2/1984 | Green |
| 4,444,181 A | 4/1984 | Wevers et al. |
| 4,454,875 A | 6/1984 | Pratt et al. |
| 4,456,006 A | 6/1984 | Wevers et al. |
| 4,485,816 A | 12/1984 | Krumme |
| 4,485,817 A | 12/1984 | Swiggett |
| 4,488,523 A | 12/1984 | Shichman |
| 4,508,253 A | 4/1985 | Green |
| 4,508,523 A | 4/1985 | Leu |
| 4,522,206 A | 6/1985 | Whipple et al. |
| 4,534,350 A | 8/1985 | Golden et al. |
| 4,535,772 A | 8/1985 | Sheehan |
| 4,566,620 A | 1/1986 | Green et al. |
| 4,570,623 A | 2/1986 | Ellison et al. |
| 4,606,343 A | 8/1986 | Conta et al. |
| 4,606,344 A | 8/1986 | Di Giovanni |
| 4,610,383 A | 9/1986 | Rothfuss et al. |
| 4,612,923 A | 9/1986 | Kronenthal |
| 4,612,933 A | 9/1986 | Brinkerhoff et al. |
| D286,442 S | 10/1986 | Korthoff et al. |
| 4,627,437 A | 12/1986 | Bedi et al. |
| 4,635,637 A | 1/1987 | Schreiber |
| 4,662,371 A | 5/1987 | Whipple et al. |
| 4,671,280 A | 6/1987 | Dorband et al. |
| 4,705,038 A | 11/1987 | Sjostrom et al. |
| 4,712,550 A | 12/1987 | Sinnett |
| 4,719,917 A | 1/1988 | Barrows et al. |
| 4,724,839 A | 2/1988 | Bedi et al. |
| 4,731,058 A | 3/1988 | Doan |
| 4,805,617 A | 2/1989 | Bedi et al. |
| 4,807,628 A | 2/1989 | Peters et al. |
| 4,852,558 A | 8/1989 | Outerbridge |
| 4,913,144 A | 4/1990 | Del Medico |
| 4,960,420 A | 10/1990 | Goble et al. |
| 4,962,877 A | 10/1990 | Hervas |
| 4,990,153 A | 2/1991 | Richards |
| 4,994,073 A | 2/1991 | Green |
| 4,995,877 A | 2/1991 | Ams et al. |
| 5,040,715 A | 8/1991 | Green et al. |
| 5,065,929 A | 11/1991 | Schulze et al. |
| 5,089,009 A | 2/1992 | Green |
| 5,108,422 A | 4/1992 | Green et al. |
| 5,114,399 A | 5/1992 | Kovalcheck |
| 5,129,570 A | 7/1992 | Schulze et al. |
| 5,143,453 A | 9/1992 | Weynant nee Girones |
| 5,203,864 A | 4/1993 | Phillips |
| 5,207,697 A | 5/1993 | Carusillo et al. |
| 5,209,756 A | 5/1993 | Seedhom et al. |
| 5,246,443 A | 9/1993 | Mai |
| 5,258,008 A | 11/1993 | Wilk |
| 5,271,543 A | 12/1993 | Grant et al. |
| RE34,519 E | 1/1994 | Fox et al. |
| 5,282,829 A | 2/1994 | Hermes |
| 5,300,081 A | 4/1994 | Young et al. |
| 5,307,976 A | 5/1994 | Olson et al. |
| 5,312,023 A | 5/1994 | Green et al. |
| 5,312,024 A | 5/1994 | Grant et al. |
| 5,313,935 A | 5/1994 | Kortenbach et al. |
| 5,318,221 A | 6/1994 | Green et al. |
| 5,326,013 A | 7/1994 | Green et al. |
| 5,330,486 A | 7/1994 | Wilk |
| 5,332,142 A | 7/1994 | Robinson et al. |
| 5,342,376 A | 8/1994 | Ruff |
| 5,350,355 A | 9/1994 | Sklar |
| 5,356,064 A | 10/1994 | Green et al. |
| 5,359,993 A | 11/1994 | Slater et al. |
| 5,364,001 A | 11/1994 | Bryan |
| 5,381,943 A | 1/1995 | Allen et al. |
| 5,383,874 A | 1/1995 | Jackson et al. |
| 5,383,880 A | 1/1995 | Hooven |
| 5,389,098 A | 2/1995 | Tsuruta et al. |
| 5,391,166 A | 2/1995 | Eggers |
| 5,395,030 A | 3/1995 | Kuramoto et al. |
| 5,395,033 A | 3/1995 | Byrne et al. |
| 5,400,267 A | 3/1995 | Denen et al. |
| 5,403,312 A | 4/1995 | Yates et al. |
| 5,405,344 A | 4/1995 | Williamson et al. |
| 5,411,508 A | 5/1995 | Bessler et al. |
| 5,413,267 A | 5/1995 | Solyntjes et al. |
| 5,431,323 A | 7/1995 | Smith et al. |
| 5,464,144 A | 11/1995 | Guy et al. |
| 5,467,911 A | 11/1995 | Tsuruta et al. |
| 5,478,344 A | 12/1995 | Stone et al. |
| 5,482,100 A | 1/1996 | Kuhar |
| 5,485,947 A | 1/1996 | Olson et al. |
| 5,487,499 A | 1/1996 | Sorrentino et al. |
| 5,497,933 A | 3/1996 | DeFonzo et al. |
| 5,500,000 A | 3/1996 | Feagin et al. |
| 5,503,320 A | 4/1996 | Webster et al. |
| 5,507,743 A | 4/1996 | Edwards et al. |
| 5,518,163 A | 5/1996 | Hooven |
| 5,518,164 A | 5/1996 | Hooven |
| 5,526,822 A | 6/1996 | Burbank et al. |
| 5,529,235 A | 6/1996 | Boiarski et al. |
| 5,531,744 A | 7/1996 | Nardella et al. |
| 5,533,661 A | 7/1996 | Main et al. |
| 5,535,934 A | 7/1996 | Boiarski et al. |
| 5,535,937 A | 7/1996 | Boiarski et al. |
| 5,558,671 A | 9/1996 | Yates |
| 5,560,532 A | 10/1996 | DeFonzo et al. |
| 5,562,239 A | 10/1996 | Boiarski et al. |
| 5,571,285 A | 11/1996 | Chow et al. |
| 5,575,799 A | 11/1996 | Bolanos et al. |
| 5,582,611 A | 12/1996 | Tsuruta et al. |
| 5,584,835 A | 12/1996 | Greenfield |
| 5,601,224 A | 2/1997 | Bishop et al. |
| 5,601,558 A | 2/1997 | Torrie et al. |
| 5,607,095 A | 3/1997 | Smith et al. |
| 5,609,285 A | 3/1997 | Grant et al. |
| 5,609,560 A | 3/1997 | Ichikawa et al. |
| 5,624,452 A | 4/1997 | Yates |
| 5,632,433 A | 5/1997 | Grant et al. |
| 5,634,926 A | 6/1997 | Jobe |
| 5,642,848 A | 7/1997 | Ludwig et al. |
| 5,653,374 A | 8/1997 | Young et al. |
| 5,658,300 A | 8/1997 | Bito et al. |
| 5,658,312 A | 8/1997 | Green et al. |
| 5,662,662 A | 9/1997 | Bishop et al. |
| 5,665,085 A | 9/1997 | Nardella |
| 5,667,513 A | 9/1997 | Torrie et al. |
| 5,667,517 A | 9/1997 | Hooven |
| 5,667,527 A | 9/1997 | Cook |
| 5,669,544 A | 9/1997 | Schulze et al. |
| 5,673,841 A | 10/1997 | Schulze et al. |
| 5,676,674 A | 10/1997 | Bolanos et al. |
| 5,680,981 A | 10/1997 | Mililli et al. |
| 5,680,982 A | 10/1997 | Schulze et al. |
| 5,690,675 A | 11/1997 | Sawyer et al. |
| 5,692,668 A | 12/1997 | Schulze et al. |
| 5,695,506 A | 12/1997 | Pike et al. |
| 5,695,524 A | 12/1997 | Kelley et al. |
| 5,702,447 A | 12/1997 | Walch et al. |
| 5,704,534 A | 1/1998 | Huitema et al. |
| 5,713,505 A | 2/1998 | Huitema |
| 5,713,896 A | 2/1998 | Nardella |
| 5,715,987 A | 2/1998 | Kelley et al. |
| 5,716,366 A | 2/1998 | Yates |
| 5,720,753 A | 2/1998 | Sander et al. |
| 5,725,529 A | 3/1998 | Nicholson et al. |
| 5,728,110 A | 3/1998 | Vidal et al. |
| 5,728,116 A | 3/1998 | Rosenman |
| 5,730,757 A | 3/1998 | Benetti et al. |
| 5,735,848 A | 4/1998 | Yates et al. |
| 5,738,474 A | 4/1998 | Blewett |
| 5,755,726 A | 5/1998 | Pratt et al. |
| 5,759,171 A | 6/1998 | Coelho et al. |
| 5,779,130 A | 7/1998 | Alesi et al. |
| 5,782,397 A | 7/1998 | Koukline |
| 5,785,713 A | 7/1998 | Jobe |
| 5,788,698 A | 8/1998 | Savornin |

(56) References Cited

U.S. PATENT DOCUMENTS

| | | | |
|---|---|---|---|
| 5,810,811 A | 9/1998 | Yates et al. |
| 5,823,066 A | 10/1998 | Huitema et al. |
| 5,829,662 A | 11/1998 | Allen et al. |
| 5,830,121 A | 11/1998 | Enomoto et al. |
| 5,849,023 A | 12/1998 | Mericle |
| 5,849,028 A | 12/1998 | Chen |
| 5,855,311 A | 1/1999 | Hamblin et al. |
| 5,861,005 A | 1/1999 | Kontos |
| 5,865,361 A | 2/1999 | Milliman et al. |
| 5,876,401 A | 3/1999 | Schulze et al. |
| 5,891,156 A | 4/1999 | Gessner et al. |
| 5,893,813 A | 4/1999 | Yamamoto |
| 5,895,396 A | 4/1999 | Day et al. |
| 5,906,607 A | 5/1999 | Taylor et al. |
| 5,911,721 A | 6/1999 | Nicholson et al. |
| 5,918,791 A | 7/1999 | Sorrentino et al. |
| 5,928,222 A | 7/1999 | Kleinerman |
| 5,944,717 A | 8/1999 | Lee et al. |
| 5,944,736 A | 8/1999 | Taylor et al. |
| 5,954,259 A | 9/1999 | Viola et al. |
| 5,961,521 A | 10/1999 | Roger |
| 5,964,394 A | 10/1999 | Robertson |
| 5,968,044 A | 10/1999 | Nicholson et al. |
| 5,976,171 A | 11/1999 | Taylor |
| 5,980,518 A | 11/1999 | Carr et al. |
| 5,980,548 A | 11/1999 | Evans et al. |
| 5,991,355 A | 11/1999 | Dahlke |
| 5,991,650 A | 11/1999 | Swanson et al. |
| 5,992,724 A | 11/1999 | Snyder |
| 5,997,552 A | 12/1999 | Person et al. |
| 6,004,335 A | 12/1999 | Vaitekunas et al. |
| 6,007,550 A | 12/1999 | Wang et al. |
| 6,010,054 A | 1/2000 | Johnson et al. |
| 6,013,077 A | 1/2000 | Harwin |
| 6,015,417 A | 1/2000 | Reynolds, Jr. |
| 6,017,354 A | 1/2000 | Culp et al. |
| 6,030,410 A | 2/2000 | Zurbrugg |
| 6,032,849 A | 3/2000 | Mastri et al. |
| 6,039,731 A | 3/2000 | Taylor et al. |
| 6,051,007 A | 4/2000 | Hogendijk et al. |
| 6,063,078 A | 5/2000 | Wittkampf |
| 6,063,095 A | 5/2000 | Wang et al. |
| 6,077,246 A | 6/2000 | Kullas et al. |
| 6,079,606 A | 6/2000 | Milliman et al. |
| 6,080,150 A | 6/2000 | Gough |
| 6,083,242 A | 7/2000 | Cook |
| 6,090,123 A | 7/2000 | Culp et al. |
| 6,092,422 A | 7/2000 | Binnig et al. |
| 6,109,500 A | 8/2000 | Alli et al. |
| 6,113,592 A | 9/2000 | Taylor |
| 6,123,702 A | 9/2000 | Swanson et al. |
| H1904 H | 10/2000 | Yates et al. |
| 6,126,058 A | 10/2000 | Adams et al. |
| 6,126,651 A | 10/2000 | Mayer |
| 6,127,811 A | 10/2000 | Shenoy et al. |
| 6,132,425 A | 10/2000 | Gough |
| 6,165,169 A | 12/2000 | Panescu et al. |
| 6,166,538 A | 12/2000 | D'Alfonso |
| 6,179,840 B1 | 1/2001 | Bowman |
| 6,187,009 B1 | 2/2001 | Herzog et al. |
| 6,187,019 B1 | 2/2001 | Stefanchik et al. |
| 6,190,401 B1 | 2/2001 | Green et al. |
| 6,193,501 B1 | 2/2001 | Masel et al. |
| 6,202,914 B1 | 3/2001 | Geiste et al. |
| 6,217,573 B1 | 4/2001 | Webster |
| 6,228,534 B1 | 5/2001 | Takeuchi et al. |
| 6,231,565 B1 | 5/2001 | Tovey et al. |
| 6,236,874 B1 | 5/2001 | Devlin et al. |
| 6,237,604 B1 | 5/2001 | Burnside et al. |
| 6,241,139 B1 | 6/2001 | Milliman et al. |
| 6,245,065 B1 | 6/2001 | Panescu et al. |
| 6,248,117 B1 | 6/2001 | Blatter |
| 6,250,532 B1 | 6/2001 | Green et al. |
| 6,258,111 B1 | 7/2001 | Ross et al. |
| 6,264,086 B1 | 7/2001 | McGuckin, Jr. |
| 6,264,087 B1 | 7/2001 | Whitman |
| 6,264,653 B1 | 7/2001 | Falwell |
| 6,281,471 B1 | 8/2001 | Smart |
| 6,288,534 B1 | 9/2001 | Starkweather et al. |
| 6,290,701 B1 | 9/2001 | Enayati |
| 6,293,943 B1 | 9/2001 | Panescu et al. |
| 6,295,330 B1 | 9/2001 | Skog et al. |
| 6,315,184 B1 | 11/2001 | Whitman |
| 6,329,778 B1 | 12/2001 | Culp et al. |
| 6,330,965 B1 | 12/2001 | Milliman et al. |
| 6,346,104 B2 | 2/2002 | Daly et al. |
| 6,355,066 B1 | 3/2002 | Kim |
| 6,364,884 B1 | 4/2002 | Bowman et al. |
| 6,387,092 B1 | 5/2002 | Burnside et al. |
| 6,388,240 B2 | 5/2002 | Schulz et al. |
| 6,402,766 B2 | 6/2002 | Bowman et al. |
| H2037 H | 7/2002 | Yates et al. |
| 6,412,279 B1 | 7/2002 | Coleman et al. |
| 6,425,903 B1 | 7/2002 | Voegele |
| 6,436,097 B1 | 8/2002 | Nardella |
| 6,436,107 B1 | 8/2002 | Wang et al. |
| 6,436,110 B2 | 8/2002 | Bowman et al. |
| 6,443,973 B1 | 9/2002 | Whitman |
| 6,447,517 B1 | 9/2002 | Bowman |
| 6,451,029 B1 * | 9/2002 | Yeatman ............. A61B 17/115 |
| | | 606/139 |
| 6,461,372 B1 | 10/2002 | Jensen et al. |
| 6,478,210 B2 | 11/2002 | Adams et al. |
| 6,497,707 B1 | 12/2002 | Bowman et al. |
| 6,505,768 B2 | 1/2003 | Whitman |
| 6,515,273 B2 | 2/2003 | Al-Ali |
| 6,524,316 B1 | 2/2003 | Nicholson et al. |
| 6,533,157 B1 | 3/2003 | Whitman |
| 6,540,751 B2 | 4/2003 | Enayati |
| 6,544,273 B1 | 4/2003 | Harari et al. |
| 6,554,852 B1 | 4/2003 | Oberlander |
| 6,562,071 B2 | 5/2003 | Jarvinen |
| 6,578,579 B2 | 6/2003 | Burnside et al. |
| 6,601,748 B1 | 8/2003 | Fung et al. |
| 6,601,749 B2 | 8/2003 | Sullivan et al. |
| 6,602,252 B2 | 8/2003 | Mollenauer |
| 6,611,793 B1 | 8/2003 | Burnside et al. |
| 6,616,821 B2 | 9/2003 | Broadley et al. |
| 6,629,986 B1 | 10/2003 | Ross et al. |
| 6,651,669 B1 | 11/2003 | Burnside |
| 6,656,177 B2 | 12/2003 | Truckai et al. |
| 6,669,073 B2 | 12/2003 | Milliman et al. |
| 6,669,705 B2 | 12/2003 | Westhaver et al. |
| 6,696,008 B2 | 2/2004 | Brandinger |
| 6,698,643 B2 | 3/2004 | Whitman |
| 6,699,177 B1 | 3/2004 | Wang et al. |
| 6,716,233 B1 | 4/2004 | Whitman |
| 6,736,085 B1 | 5/2004 | Esnouf |
| 6,792,390 B1 | 9/2004 | Burnside et al. |
| 6,793,652 B1 | 9/2004 | Whitman et al. |
| 6,817,508 B1 | 11/2004 | Racenet et al. |
| 6,830,174 B2 | 12/2004 | Hillstead et al. |
| 6,843,403 B2 | 1/2005 | Whitman |
| 6,846,307 B2 | 1/2005 | Whitman et al. |
| 6,846,308 B2 | 1/2005 | Whitman et al. |
| 6,846,309 B2 | 1/2005 | Whitman et al. |
| 6,849,071 B2 | 2/2005 | Whitman et al. |
| 6,861,639 B2 | 3/2005 | Al-Ali |
| 6,872,214 B2 | 3/2005 | Sonnenschein et al. |
| 6,899,538 B2 | 5/2005 | Matoba |
| 6,900,004 B2 | 5/2005 | Satake |
| 6,905,057 B2 | 6/2005 | Swayze et al. |
| 6,926,636 B2 | 8/2005 | Luper |
| 6,953,139 B2 | 10/2005 | Milliman et al. |
| 6,959,852 B2 | 11/2005 | Shelton, IV et al. |
| 6,964,363 B2 | 11/2005 | Wales et al. |
| 6,979,328 B2 | 12/2005 | Baerveldt et al. |
| 6,981,628 B2 | 1/2006 | Wales |
| 6,981,941 B2 | 1/2006 | Whitman et al. |
| 6,988,649 B2 | 1/2006 | Shelton, IV et al. |
| 7,000,819 B2 | 2/2006 | Swayze et al. |
| 7,032,798 B2 | 4/2006 | Whitman et al. |
| 7,044,353 B2 | 5/2006 | Mastri et al. |
| 7,048,687 B1 | 5/2006 | Reuss et al. |

(56) References Cited

U.S. PATENT DOCUMENTS

| | | |
|---|---|---|
| 7,055,731 B2 | 6/2006 | Shelton, IV et al. |
| 7,059,508 B2 | 6/2006 | Shelton, IV et al. |
| 7,077,856 B2 | 7/2006 | Whitman |
| 7,083,075 B2 | 8/2006 | Swayze et al. |
| 7,097,089 B2 | 8/2006 | Marczyk |
| 7,111,769 B2 | 9/2006 | Wales et al. |
| 7,118,564 B2 | 10/2006 | Ritchie et al. |
| 7,122,029 B2 | 10/2006 | Koop et al. |
| 7,128,253 B2 | 10/2006 | Mastri et al. |
| 7,128,254 B2 | 10/2006 | Shelton, IV et al. |
| 7,140,528 B2 | 11/2006 | Shelton, IV |
| 7,143,924 B2 | 12/2006 | Scirica et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,186,966 B2 | 3/2007 | Al-Ali |
| 7,193,519 B2 | 3/2007 | Root et al. |
| 7,217,269 B2 | 5/2007 | El-Galley et al. |
| 7,220,232 B2 | 5/2007 | Suorsa et al. |
| 7,240,817 B2 | 7/2007 | Higuchi |
| 7,241,270 B2 | 7/2007 | Horzewski et al. |
| 7,246,734 B2 | 7/2007 | Shelton, IV |
| 7,303,108 B2 | 12/2007 | Shelton, IV |
| 7,328,828 B2 | 2/2008 | Ortiz et al. |
| 7,335,169 B2 | 2/2008 | Thompson et al. |
| 7,364,061 B2 | 4/2008 | Swayze et al. |
| 7,380,695 B2 | 6/2008 | Doll et al. |
| 7,380,696 B2 | 6/2008 | Shelton, IV et al. |
| 7,404,508 B2 | 7/2008 | Smith et al. |
| 7,416,101 B2 | 8/2008 | Shelton, IV et al. |
| 7,419,080 B2 | 9/2008 | Smith et al. |
| 7,422,136 B1 | 9/2008 | Marczyk |
| 7,422,139 B2 | 9/2008 | Shelton, IV et al. |
| 7,431,188 B1 | 10/2008 | Marczyk |
| 7,431,189 B2 | 10/2008 | Shelton, IV et al. |
| 7,434,715 B2 | 10/2008 | Shelton, IV et al. |
| 7,441,684 B2 | 10/2008 | Shelton, IV et al. |
| 7,448,525 B2 | 11/2008 | Shelton, IV et al. |
| 7,461,767 B2 | 12/2008 | Viola et al. |
| 7,464,846 B2 | 12/2008 | Shelton, IV et al. |
| 7,464,847 B2 | 12/2008 | Viola et al. |
| 7,464,849 B2 | 12/2008 | Shelton, IV et al. |
| 7,481,348 B2 | 1/2009 | Marczyk |
| 7,487,899 B2 | 2/2009 | Shelton, IV et al. |
| 7,549,563 B2 | 6/2009 | Mather et al. |
| 7,552,854 B2 | 6/2009 | Wixey et al. |
| 7,556,185 B2 | 7/2009 | Viola |
| 7,568,603 B2 | 8/2009 | Shelton, IV et al. |
| 7,637,409 B2 | 12/2009 | Marczyk |
| 7,641,093 B2 | 1/2010 | Doll et al. |
| 7,644,848 B2 | 1/2010 | Swayze et al. |
| 7,648,055 B2 | 1/2010 | Marczyk |
| 7,670,334 B2 | 3/2010 | Hueil et al. |
| 7,694,809 B2 | 4/2010 | Garbini et al. |
| 7,721,931 B2 | 5/2010 | Shelton, IV et al. |
| 7,740,159 B2 | 6/2010 | Shelton, IV et al. |
| 7,753,248 B2 | 7/2010 | Viola |
| 7,757,925 B2 | 7/2010 | Viola et al. |
| 7,766,207 B2 | 8/2010 | Mather et al. |
| 7,766,210 B2 | 8/2010 | Shelton, IV et al. |
| 7,770,775 B2 | 8/2010 | Shelton, IV et al. |
| 7,784,663 B2 | 8/2010 | Shelton, IV |
| 7,815,090 B2 | 10/2010 | Marczyk |
| 7,823,760 B2 | 11/2010 | Zemlok et al. |
| 7,845,534 B2 | 12/2010 | Viola et al. |
| 7,870,989 B2 | 1/2011 | Viola et al. |
| 7,886,953 B2 | 2/2011 | Schwemberger et al. |
| 7,887,530 B2 | 2/2011 | Zemlok et al. |
| 7,905,897 B2 | 3/2011 | Whitman et al. |
| 7,909,221 B2 | 3/2011 | Viola et al. |
| 7,922,063 B2 | 4/2011 | Zemlok et al. |
| 7,931,660 B2 | 4/2011 | Aranyi et al. |
| 7,950,560 B2 | 5/2011 | Zemlok et al. |
| 7,955,352 B2 | 6/2011 | McEwen et al. |
| 8,006,885 B2 | 8/2011 | Marczyk |
| 8,006,887 B2 | 8/2011 | Marczyk |
| 8,011,551 B2 | 9/2011 | Marczyk et al. |
| 8,020,742 B2 | 9/2011 | Marczyk |
| 8,025,199 B2 | 9/2011 | Whitman et al. |
| 8,038,044 B2 | 10/2011 | Viola |
| 8,052,024 B2 | 11/2011 | Viola et al. |
| 8,066,721 B2 | 11/2011 | Kortenbach et al. |
| 8,074,858 B2 | 12/2011 | Marczyk |
| 8,092,493 B2 | 1/2012 | Marczyk |
| 8,128,645 B2 | 3/2012 | Sonnenschein et al. |
| 8,132,705 B2 | 3/2012 | Viola et al. |
| 8,157,150 B2 | 4/2012 | Viola et al. |
| 8,186,555 B2 | 5/2012 | Shelton, IV et al. |
| 8,201,721 B2 | 6/2012 | Zemlok et al. |
| 8,210,412 B2 | 7/2012 | Marczyk |
| 8,225,981 B2 * | 7/2012 | Criscuolo ............ A61B 17/115 |
| | | 227/19 |
| 8,240,536 B2 | 8/2012 | Marczyk |
| 8,240,537 B2 | 8/2012 | Marczyk |
| 8,267,924 B2 | 9/2012 | Zemlok et al. |
| 8,328,823 B2 | 12/2012 | Aranyi et al. |
| 8,348,125 B2 | 1/2013 | Viola et al. |
| 8,685,004 B2 | 4/2014 | Zemlock et al. |
| 8,770,460 B2 * | 7/2014 | Belzer ................ A61B 17/1155 |
| | | 227/179.1 |
| 9,192,381 B2 | 11/2015 | Marczyk |
| 9,265,503 B2 * | 2/2016 | Vestweber ........... A61B 17/105 |
| 9,364,222 B2 | 6/2016 | Zemlok et al. |
| 9,370,360 B2 | 6/2016 | Marczyk |
| 9,370,361 B2 | 6/2016 | Viola et al. |
| 9,433,415 B2 | 9/2016 | Marczyk et al. |
| 9,480,492 B2 | 11/2016 | Aranyi et al. |
| 9,585,659 B2 | 3/2017 | Viola et al. |
| 10,441,288 B2 * | 10/2019 | Vestweber ........... A61B 17/115 |
| 10,492,814 B2 | 12/2019 | Snow et al. |
| 10,722,222 B2 | 7/2020 | Aranyi |
| 2002/0103489 A1 | 8/2002 | Ku |
| 2002/0111641 A1 | 8/2002 | Peterson et al. |
| 2002/0165541 A1 | 11/2002 | Whitman |
| 2003/0090201 A1 | 5/2003 | Peng |
| 2003/0114851 A1 | 6/2003 | Truckai et al. |
| 2003/0120306 A1 | 6/2003 | Burbank et al. |
| 2004/0232201 A1 | 11/2004 | Wenchell et al. |
| 2005/0006429 A1 | 1/2005 | Wales et al. |
| 2005/0010235 A1 | 1/2005 | VanDusseldorp |
| 2005/0131390 A1 | 6/2005 | Heinrich et al. |
| 2005/0139636 A1 | 6/2005 | Schwemberger et al. |
| 2005/0177176 A1 | 8/2005 | Gerbi et al. |
| 2005/0192609 A1 | 9/2005 | Whitman et al. |
| 2005/0247753 A1 | 11/2005 | Kelly et al. |
| 2006/0000867 A1 | 1/2006 | Shelton et al. |
| 2006/0108393 A1 * | 5/2006 | Heinrich .......... A61B 17/00491 |
| | | 227/179.1 |
| 2007/0023477 A1 | 2/2007 | Whitman et al. |
| 2007/0029363 A1 | 2/2007 | Popov |
| 2007/0084897 A1 | 4/2007 | Shelton et al. |
| 2007/0102472 A1 | 5/2007 | Shelton |
| 2007/0175949 A1 | 8/2007 | Shelton et al. |
| 2007/0175950 A1 | 8/2007 | Shelton et al. |
| 2007/0175951 A1 | 8/2007 | Shelton et al. |
| 2007/0175955 A1 | 8/2007 | Shelton et al. |
| 2007/0219563 A1 | 9/2007 | Voegele |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0135600 A1 | 6/2008 | Hiranuma et al. |
| 2008/0169329 A1 | 7/2008 | Shelton et al. |
| 2008/0185419 A1 | 8/2008 | Smith et al. |
| 2008/0197167 A1 | 8/2008 | Viola et al. |
| 2008/0255413 A1 | 10/2008 | Zemlok et al. |
| 2008/0255607 A1 | 10/2008 | Zemlok |
| 2009/0018624 A1 | 1/2009 | Levinson et al. |
| 2009/0090201 A1 | 4/2009 | Viola |
| 2009/0090763 A1 | 4/2009 | Zemlok et al. |
| 2009/0216248 A1 | 8/2009 | Uenohara et al. |
| 2010/0163598 A1 * | 7/2010 | Belzer ................ A61B 17/1155 |
| | | 227/181.1 |
| 2010/0200636 A1 | 8/2010 | Zemlok et al. |

(56) References Cited

U.S. PATENT DOCUMENTS

| | | |
|---|---|---|
| 2010/0312257 A1 | 12/2010 | Aranyi |
| 2010/0320254 A1 | 12/2010 | Zemlok et al. |
| 2011/0034910 A1 | 2/2011 | Ross et al. |
| 2011/0062211 A1 | 3/2011 | Ross et al. |
| 2011/0168757 A1 | 7/2011 | Viola et al. |
| 2011/0172681 A1 | 7/2011 | Aranyi et al. |
| 2011/0190738 A1 | 8/2011 | Zemlok et al. |
| 2011/0301579 A1 | 12/2011 | Marczyk et al. |
| 2011/0303735 A1 | 12/2011 | Marczyk |
| 2012/0055972 A1 | 3/2012 | Marczyk |
| 2012/0074197 A1 | 3/2012 | Marczyk |
| 2012/0175400 A1 | 7/2012 | Viola et al. |
| 2012/0193393 A1 | 8/2012 | Viola et al. |
| 2012/0198288 A1 | 8/2012 | Njo et al. |
| 2012/0220989 A1 | 8/2012 | Zemlok et al. |
| 2012/0223121 A1 | 9/2012 | Viola et al. |
| 2012/0241494 A1 | 9/2012 | Marczyk |
| 2012/0277790 A1 | 11/2012 | Zemlok et al. |
| 2012/0298718 A1 | 11/2012 | Marczyk |
| 2012/0298720 A1 | 11/2012 | Marczyk |
| 2014/0074130 A1 | 3/2014 | Vestweber |

FOREIGN PATENT DOCUMENTS

| | | |
|---|---|---|
| EP | 0537570 A2 | 4/1993 |
| EP | 0647431 A2 | 4/1995 |
| EP | 0738501 A1 | 10/1996 |
| EP | 0770354 A1 | 5/1997 |
| EP | 1070487 A2 | 1/2001 |
| EP | 1201196 A1 | 5/2002 |
| EP | 1658817 A1 | 5/2006 |
| EP | 1813203 A2 | 8/2007 |
| EP | 3023077 A1 | 5/2016 |
| FR | 2 849 589 A1 | 7/2004 |
| WO | 9414129 A1 | 6/1994 |
| WO | 9729694 A1 | 8/1997 |
| WO | 9740760 A1 | 11/1997 |
| WO | 9837825 A1 | 9/1998 |
| WO | 1999/52489 A1 | 10/1999 |
| WO | 0234140 A2 | 5/2002 |
| WO | 03026511 A1 | 4/2003 |
| WO | 03030743 A2 | 4/2003 |
| WO | 2004032760 A2 | 4/2004 |
| WO | 2007030753 A2 | 3/2007 |
| WO | 2007/114868 A2 | 10/2007 |
| WO | 2007118179 A2 | 10/2007 |
| WO | 2007014355 A3 | 4/2009 |
| WO | 2009143092 A1 | 11/2009 |

OTHER PUBLICATIONS

Abridged Data Sheet, "DeepCover Secure Authenticator with 1-Wire SHA-256 and 512-Bit User EEPROM", Maxim Integrated Products, Inc. pp. 1-4; 42; Dec. 2012.

Data Sheet "DS28E15-1-Sire SHA-256 Secure Authenticator with 512-Bit User EEPROM"; IC-ON-LINE, Electronic Component Manufacturers, pp. 1-2; Aug. 2013.

Extended European Search Report for application No. 21155398.7 dated Jun. 9, 2021.

* cited by examiner

IRRIGATING SURGICAL APPARATUS WITH POSITIVE PRESSURE FLUID

CROSS-REFERENCE TO RELATED APPLICATIONS

This application claims the benefit of and priority to U.S. Provisional Patent Application Ser. No. 62/971,521 filed Feb. 7, 2020, the entire disclosure of which is incorporated by reference herein.

TECHNICAL FIELD

This application relates to surgical apparatus and more particularly, to surgical systems, devices, and methods for irrigating surgical instruments.

BACKGROUND

Surgical apparatus are employed by clinicians to effectuate surgical procedures on patients. For example, surgical stapling apparatus are employed by surgeons to sequentially or simultaneously apply one or more rows of fasteners, e.g., staples or two-part fasteners, to body tissue for the purpose of joining segments of body tissue together. When the surgical stapling apparatus is actuated, or "fired," staple drive members in one of the jaws push the surgical staples through the body tissue and into an anvil in the opposite jaw which forms the staples. If body tissue is to be removed or separated, a knife blade can be provided in one of the jaws of the apparatus to cut the body tissue between the lines of staples. Often, it is desirable to reuse such surgical apparatus after being exposed to blood, tissue, soil or other contaminants during a surgical procedure. Accordingly, reusable surgical apparatus are cleaned prior to reuse.

SUMMARY

In an aspect of this disclosure, a surgical instrument includes an elongated tubular body portion and an irrigation assembly. The elongated tubular body portion extends distally to an end effector and defines an interior cavity. The irrigation assembly includes an inlet port and a shaft assembly supported within the elongated tubular body portion. The inlet port and the shaft assembly are disposed in fluid communication with one another to deliver fluid from the inlet port into the interior cavity of the elongated tubular body portion to irrigate the interior cavity with positive fluid pressure.

In aspects, the elongated tubular body portion may include one or more egress orifices that are configured to enable fluid to exit from the elongated tubular body portion.

In various aspects, the shaft assembly may include an inner shaft and an outer shaft. The inner shaft may be supported within the outer shaft.

In some aspects, the elongated tubular body portion may be configured to removably couple to a handle assembly that operates the end effector. The elongated tubular body portion may support a housing assembly on a proximal end portion of elongated tubular body portion such that a proximal end portion of the housing assembly couples to a distal end portion of the handle assembly to removably couple the elongated tubular body portion to the handle assembly. The housing assembly may include an outer housing and an inner housing. The outer housing may be independent of the inner housing and may support the inlet port. The inner housing may support a proximal end portion of the shaft assembly.

The outer housing may define a first fluid channel therethrough that is in fluid communication with the inlet port. The inner housing may define a second fluid channel therethrough that is in fluid communication with the first fluid channel. The second fluid channel may be disposed in fluid communication with a third fluid channel defined within the shaft assembly.

In certain aspects, a relief conduit may be coupled to the end effector and positioned to remove excess fluid delivered to the elongated tubular body portion.

According to one aspect, a surgical instrument system includes a fluid source, an elongated tubular body portion, and an irrigation assembly. The elongated tubular body portion defines an interior cavity. The irrigation assembly is coupled to the elongated tubular body portion. The irrigation assembly includes an inlet port and a shaft assembly supported by the elongated tubular body portion. The inlet port and the shaft assembly are in fluid communication with one another to deliver fluid from the fluid source and into the interior cavity of the elongated tubular body portion via the inlet port to irrigate the interior cavity with positive fluid pressure.

In aspects, the inlet port and the shaft assembly may be in fluid communication via one or more fluid channels extending between the inlet port and the shaft assembly.

In various aspects, the inner shaft may be disposed in fluid communication with the one or more fluid channels.

In some aspects, a relief conduit may be coupled to the elongated tubular body portion and positioned to return excess fluid delivered to the elongated tubular body portion back to the fluid source.

According to yet another aspect, a surgical stapling system includes a fluid source, a surgical stapling instrument, and an irrigation assembly. The surgical stapling instrument includes an elongated tubular body portion defining an interior cavity. The irrigation assembly is in fluid communication with the fluid source and coupled to the elongated tubular body portion. The irrigation assembly includes an inlet port in fluid communication with the interior cavity of the elongated tubular body portion to deliver fluid into the interior cavity and irrigate the interior cavity with positive fluid pressure.

In aspects, the surgical stapling system further includes a shaft assembly. The shaft assembly including an inner shaft and an outer shaft. The inner shaft supported within the outer shaft, wherein the inlet port and the inner shaft are in fluid communication via one or more fluid channels extending between the inlet port and the inner shaft.

In certain aspects, a relief conduit is coupled to the elongated tubular body portion and positioned to enable excess fluid within the elongated tubular body portion to exit from the elongated tubular body portion.

BRIEF DESCRIPTION OF THE DRAWINGS

The above and other aspects, features, and advantages of this disclosure will be apparent in light of the following detailed description when taken in conjunction with the accompanying drawings, which are incorporated in and constitute a part of this specification, wherein.

DETAILED DESCRIPTION

Aspects of this disclosure will now be described in detail with reference to the drawing figures wherein like reference numerals identify similar or identical elements. Throughout this description, the term "proximal" refers to a portion of a structure, or component thereof, that is closer to a user, and the term "distal" refers to a portion of the structure, or component thereof, that is farther from the user. Directional reference terms, such as "top," "bottom," "side," and the like, are used to ease description of the aspects and are not intended to have any limiting effect on the ultimate orientation of a structure or any part thereof. In the following description, well-known functions or constructions are not described in detail to avoid obscuring this disclosure in unnecessary detail.

Figure 1:
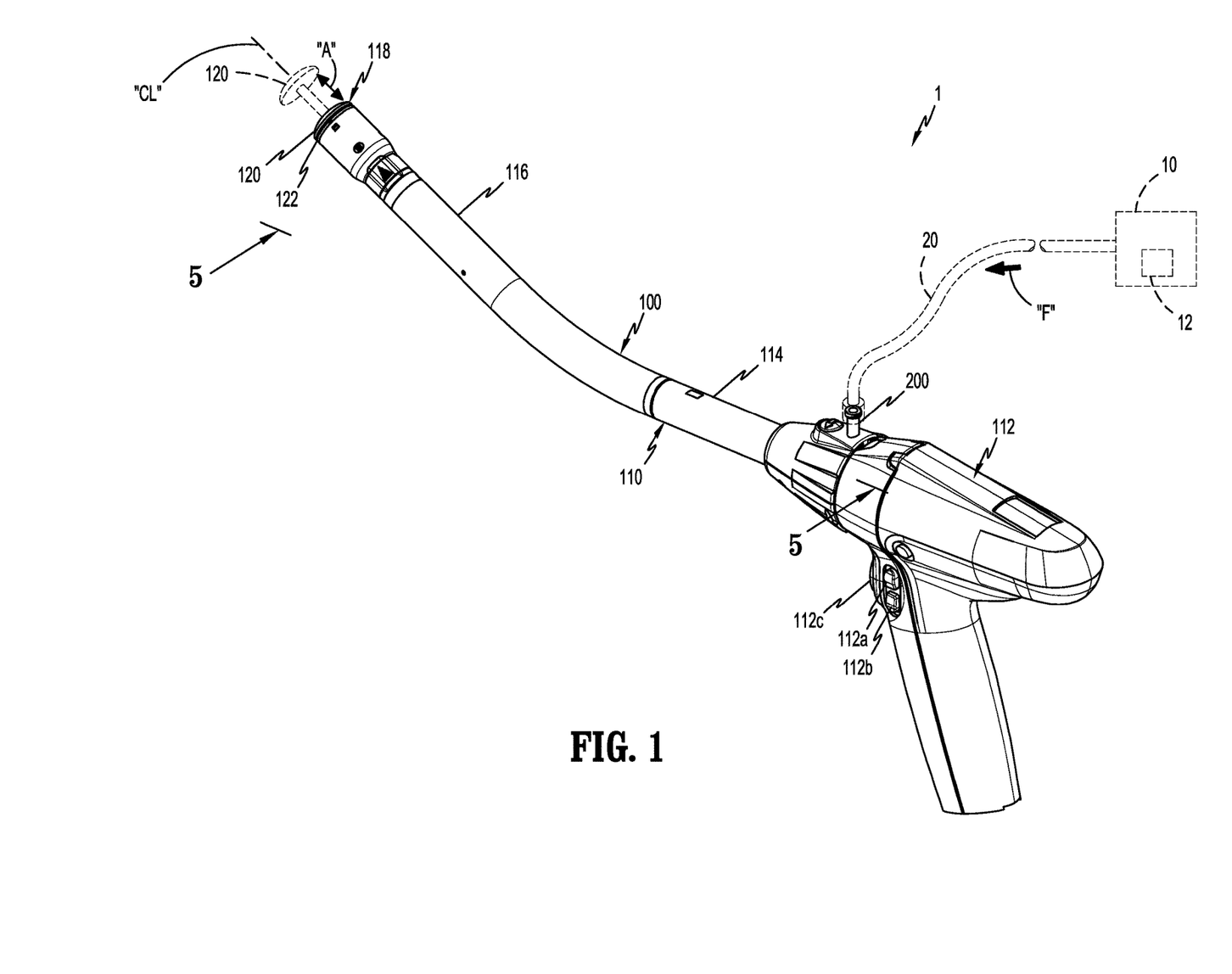
FIG. 1 is a perspective view of a surgical system in accordance with the principles of this disclosure.

Referring now to FIG. 1, a surgical system 1, in accordance with this disclosure, includes a fluid source 10 and a surgical instrument 100 disposed in fluid communication with one another via a fluid conduit 20. Fluid source 10 can include any suitable fluid "F" such as saline or the like and may support one or more pumps 12 to pump fluid "F" from fluid source 10 and/or back into fluid source 10. Surgical instrument 100 is described herein as a surgical stapling apparatus 110, but may include any suitable surgical instrument such as a clip applier, grasper, stitching device, endoscope, energy-based device (e.g., a bipolar or monopolar forceps), or the like. Moreover, although described herein in connection with a powered circular stapling apparatus for brevity, surgical stapling apparatus 110 can include any powered, manual, or robotically-controlled surgical stapling apparatus such as a laparoscopic stapler, a transverse stapler, or an open stapler.

Briefly, surgical stapling apparatus 110 of surgical system 1 generally includes a handle assembly 112 and an elongated tubular body portion 114 that extends distally from handle assembly 112 and defines a center line "CL" therealong. Elongated tubular body portion 114, which may be in the form of an adapter assembly as shown in FIG. 1, can be selectively removable from handle assembly 112, or permanently fixed thereto. Elongated tubular body portion 114 defines an internal cavity 114a and includes any number of egress orifices 114b (see FIG. 5) configured to enable fluid "F" from fluid source 10 to exit from elongated tubular body portion 114. Elongated tubular body portion 114 may include a surgical loading unit 116 that is selectively attachable to a distal portion of elongated tubular body portion 114. An end effector 118 is supported on a distal end portion of surgical loading unit 116. Surgical loading unit 116, or portions thereof (e.g., end effector 118), may be removable and/or replaceable. For example, end effector 118 includes first jaw member in the form of an anvil assembly 120 and a second jaw member in the form of a staple cartridge assembly 122. The end effector 118, or portions thereof, may be permanently affixed to elongated tubular body portion 114 or may be detachable with respect to elongated tubular body portion 114 and thus, replaceable with a new end effector 118. As indicated by arrows "A," anvil assembly 120 is movable relative to staple cartridge assembly 122 between an open position in which anvil and staple cartridge assemblies 120, 122 are spaced apart with respect to each other (shown in phantom in FIG. 1) and a closed position in which anvil and staple cartridge assemblies 120, 122 are substantially adjacent each other for selectively clamping tissue between anvil and staple cartridge assemblies 120, 122 as seen in FIG. 1.

Handle assembly 112 of surgical stapling apparatus 110 includes any number of actuators 12a, 12b, 12c to facilitate a firing of end effector 118 and/or movement of the end effector 118, or portions thereof, relative to handle assembly 112 such as an opening and/or closing of anvil and/or cartridge assemblies 120, 122 to clamp tissue therebetween. End effector 118 is configured to apply lines of staples (not shown) to tissue captured between the anvil and staple cartridge assemblies 120, 122 when fired, for example, upon actuation of actuator 12c.

For a detailed description of the structure and function of exemplary surgical stapling apparatus, one or more components of which may be included, or modified for use with the disclosed aspects, reference may be made to U.S. Pat. Nos. 8,256,656; 8,1571,152; 7,819,896; 7,334,717; 7,128,253; 5,964,394; and 5,915,616, the entire contents of each of which is incorporated herein by reference.

With reference also to FIGS. 2-6, surgical stapling apparatus 110 includes an irrigation assembly 200 supported by elongated tubular body portion 114 to incorporate a continuous flow of fluid "F" from fluid source 10 through elongated tubular body portion 114 to inhibit soil ingress, to aid in introduction of surgical stapling apparatus 110 into patient (e.g., lubrication), and/or to tests for leaks upon effectuating an anastomosis with surgical stapling apparatus 110. In particular, irrigation assembly 200 is configured to facilitate an application of irrigation by passing fluid "F" from fluid source 10 through interior cavity 114a (FIG. 5) of elongated tubular body portion 114 to create a positive pressure gradient and discourage foreign matter such as soil and contaminants from entering elongated tubular body portion 114, thereby improving the cleanability of surgical stapling apparatus 110 for subsequent procedures or reuse.

Figure 2:
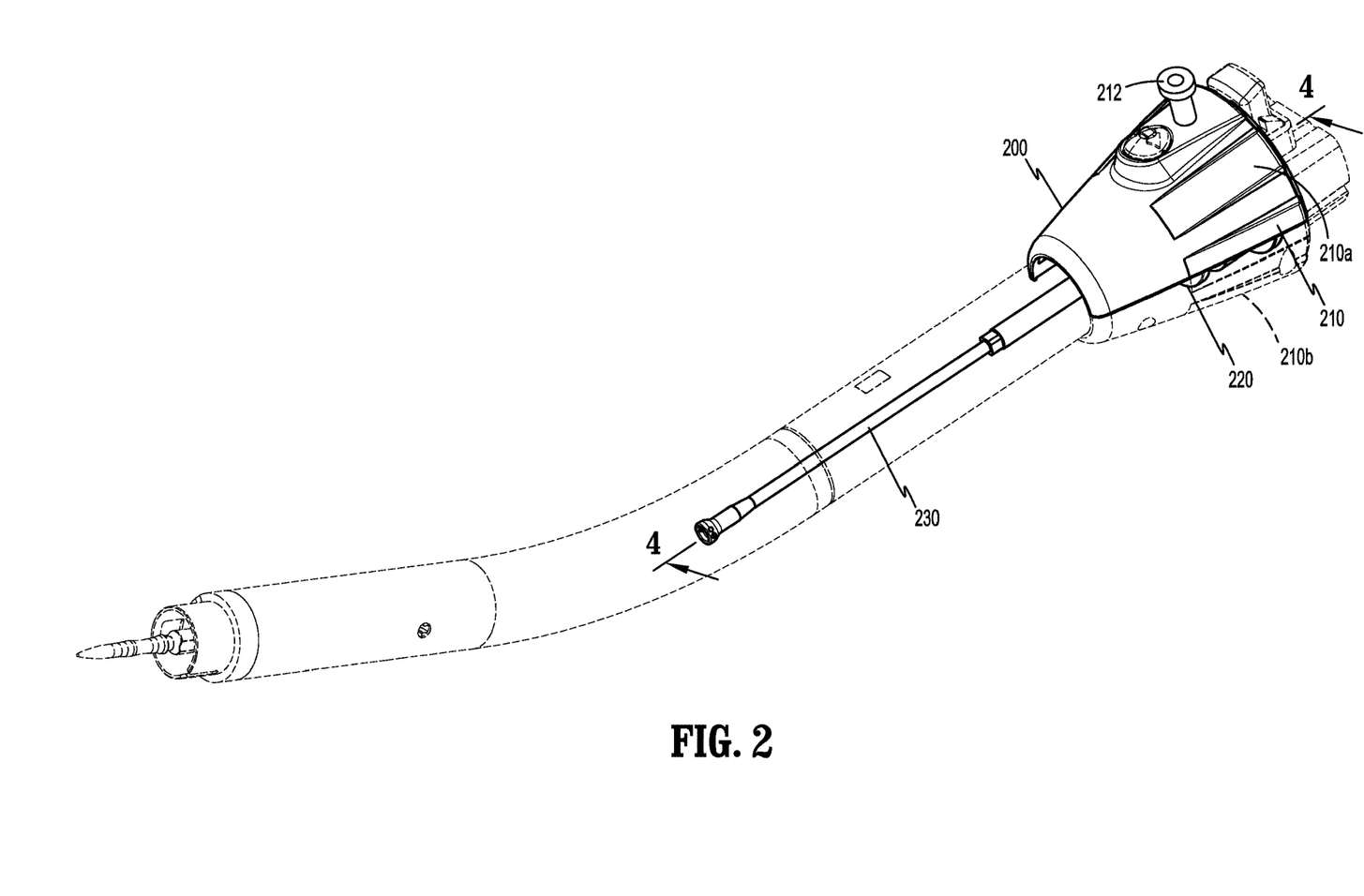
FIG. 2 is an enlarged view of an adapter of a surgical instrument of the surgical system of FIG. 1 with portions of the adapter shown in phantom for clarity.
Figure 3:
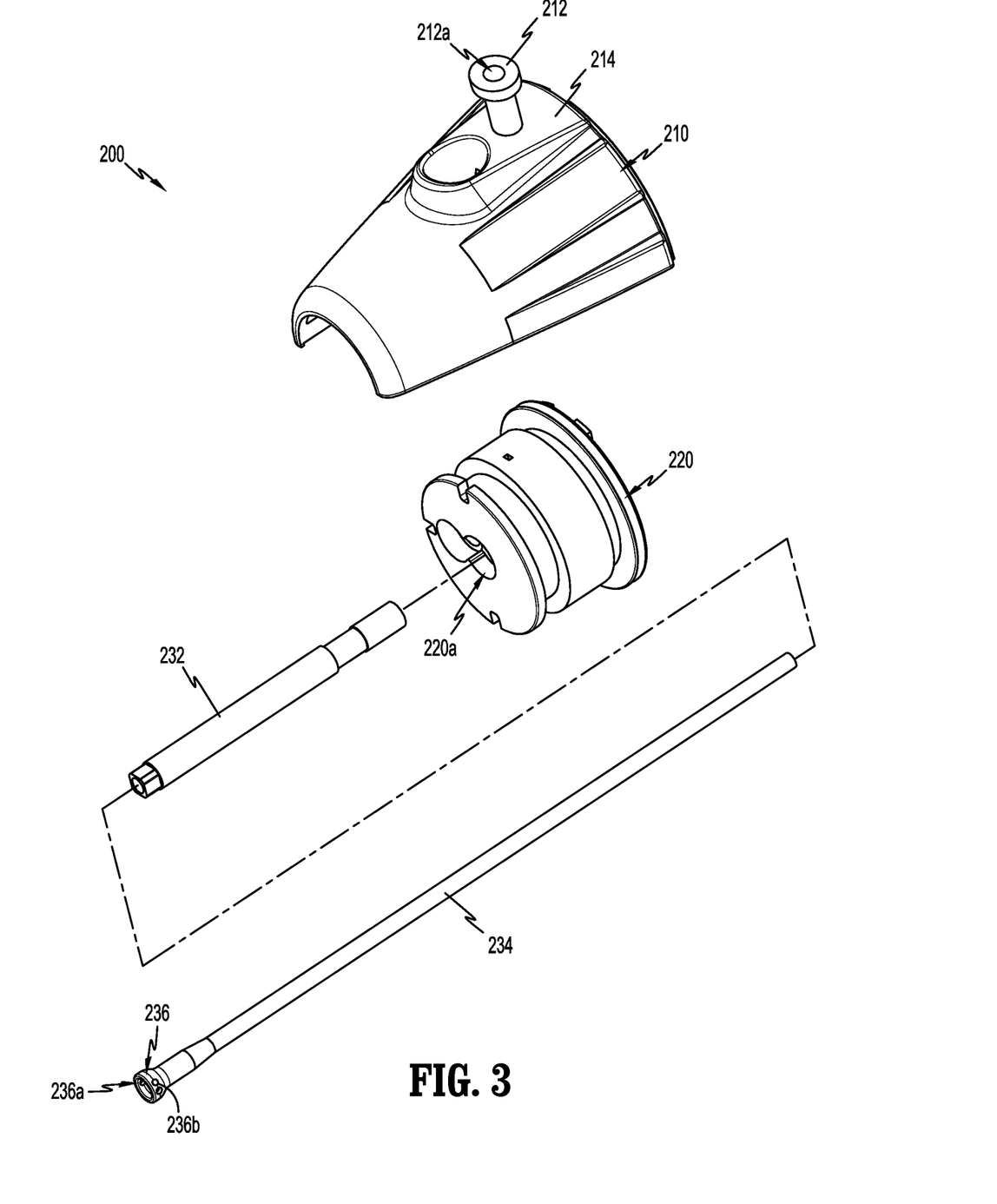
FIG. 3 is a perspective view, with parts separated, of an irrigation assembly of the adapter of FIG. 2.
Figure 4:
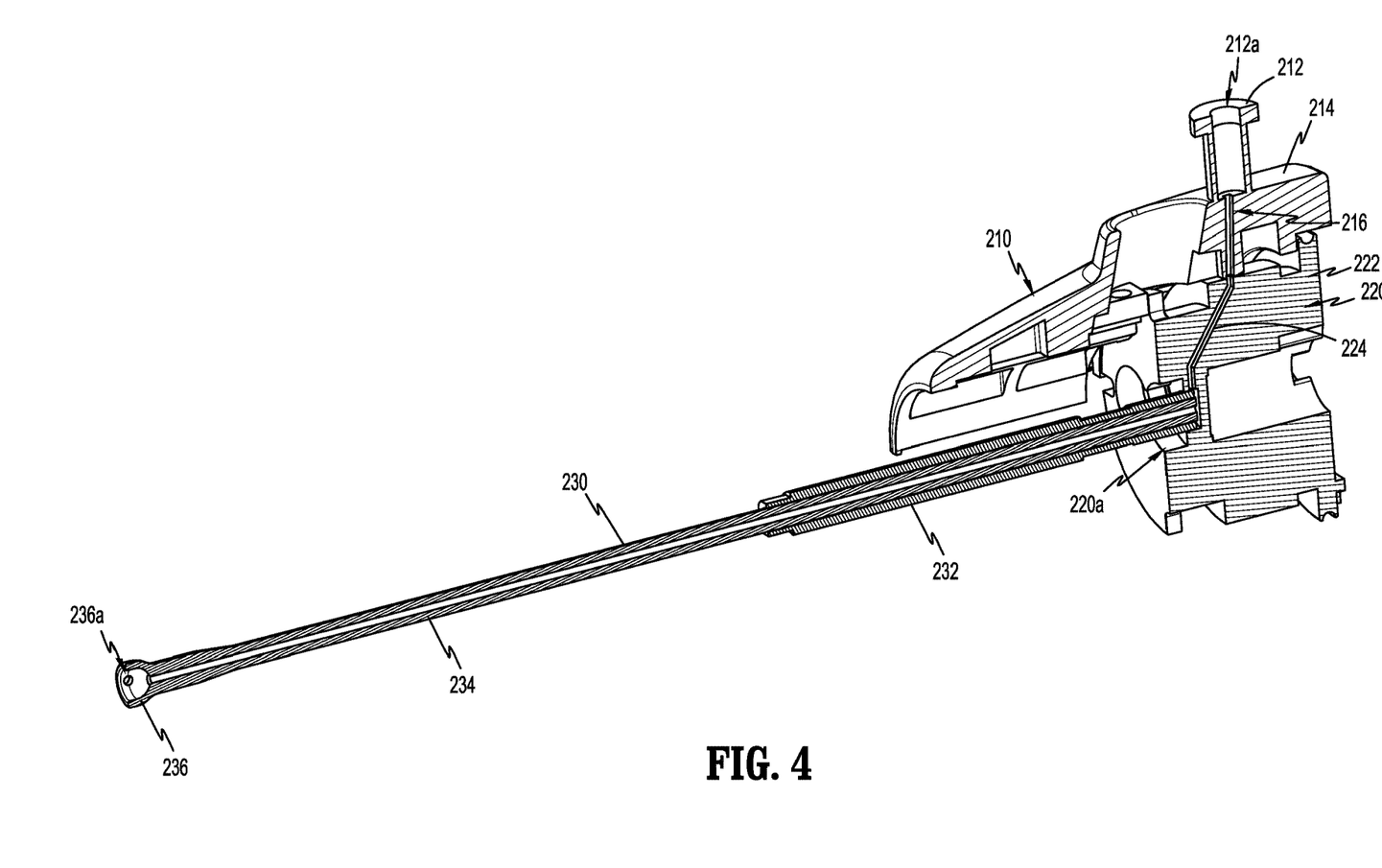
FIG. 4 is an enlarged, cross-sectional view of the irrigation assembly of FIG. 3 as taken along section line 4-4 shown in FIG. 2.

Irrigation assembly 200 of surgical stapling apparatus 110 includes an outer housing 210, an inner housing 220, and a shaft assembly 230 supported by elongated tubular body portion 114. Outer housing 210, inner housing 220, and shaft assembly 230 are disposed in fluid communication with one another to enable fluid "F" to be continuously delivered into interior cavity 114a of elongated tubular body portion 114 from fluid source 10 under positive pressure.

Outer housing 210 of irrigation assembly 200 is supported on a proximal end portion of elongated tubular body portion 114 to enable the proximal end portion of elongated tubular body portion 114 to selectively couple to a distal end portion of handle assembly 112 of surgical stapling apparatus 110. Outer housing 210 includes a first portion 210a and a second portion 210b that couple together on the proximal end portion of elongated tubular body portion 114. Outer housing 210 further includes an inlet port 212 that extends from an outer sidewall 214 of outer housing 210. Inlet port 212 couples to fluid source 10 via fluid conduit 20 and is configured to enable fluid "F" from fluid source 10 to be received into elongated tubular body portion 114 via a passage 212a extending through inlet port 212. Inlet port 212 further includes a coupling end 212b that connects with fluid conduit 20. To facilitate connection to fluid conduit 20, coupling end 212b of inlet port 212 can have any suitable arrangement such as a threaded outer surface for a threaded coupling, luer lock, magnetic, friction-fit, etc. Outer housing 210 defines a first fluid channel 216 that extends through outer sidewall 214 of outer housing 210 and is disposed in fluid communication with passage 212a of inlet port 212.

Inner housing 220 of irrigation assembly 200 is received within outer housing 210 of irrigation assembly 200. Inner housing 220 defines a distal bore 220a that receives a proximal end portion of shaft assembly 230 of irrigation assembly 200 therein to support shaft assembly 230 within the interior cavity 114a of elongated tubular body portion 114. Inner housing 220 has a sidewall 222 that defines a second fluid conduit 224 therethrough. Second fluid conduit 224 is disposed in fluid communication with first fluid conduit 216 of outer housing 210 and extends into distal bore 220a of inner housing 220 to establish fluid communication with a proximal end portion of shaft assembly 230. In aspects, distal bore 220a may be disposed in fluid communication with interior cavity 114c of elongated tubular body portion 114 to enable fluid "F" to release into interior cavity 114c adjacent to a proximal end portion of shaft assembly 230.

Shaft assembly 230 of irrigation assembly 200 includes an outer shaft 232 and an inner shaft 234 received within outer shaft 232. Outer shaft 232 of shaft assembly 230 supports inner shaft 234 of shaft assembly 230 within distal bore 220a of inner housing 220. Inner shaft 234 defines a third fluid conduit 234a therethrough that is disposed in fluid communication with second fluid conduit 224 of inner housing 220 via distal bore 220a. Inner shaft 234 extends distally beyond outer shaft 232 to a distal coupling 236 that couples to a drive mechanism 114c of elongated tubular body portion 114 for operating end effector 118 thereof. Distal coupling 236 may have a cupped or flared opening 236a, which may function as a U-joint to facilitate coupling to drive mechanism 114c of elongated tubular body portion 114 (e.g., pinned thereto). Distal coupling 236 also facilitates release of fluid "F" into the interior cavity 114c of elongated tubular body portion 114 at a distal end portion of shaft assembly 230. Distal coupling 236 can include any number of sidewall openings 236b to facilitate release of fluid "F" into interior cavity 114c of elongated tubular body portion 114. In aspects, inner and/or outer shafts 232, 234 may include any number of sidewall openings therethrough (such as sidewall opening 236b) at one or more longitudinal positions therealong to facilitate fluid release at different locations along lengths of inner and/or outer shafts 232, 234.

Figure 5:
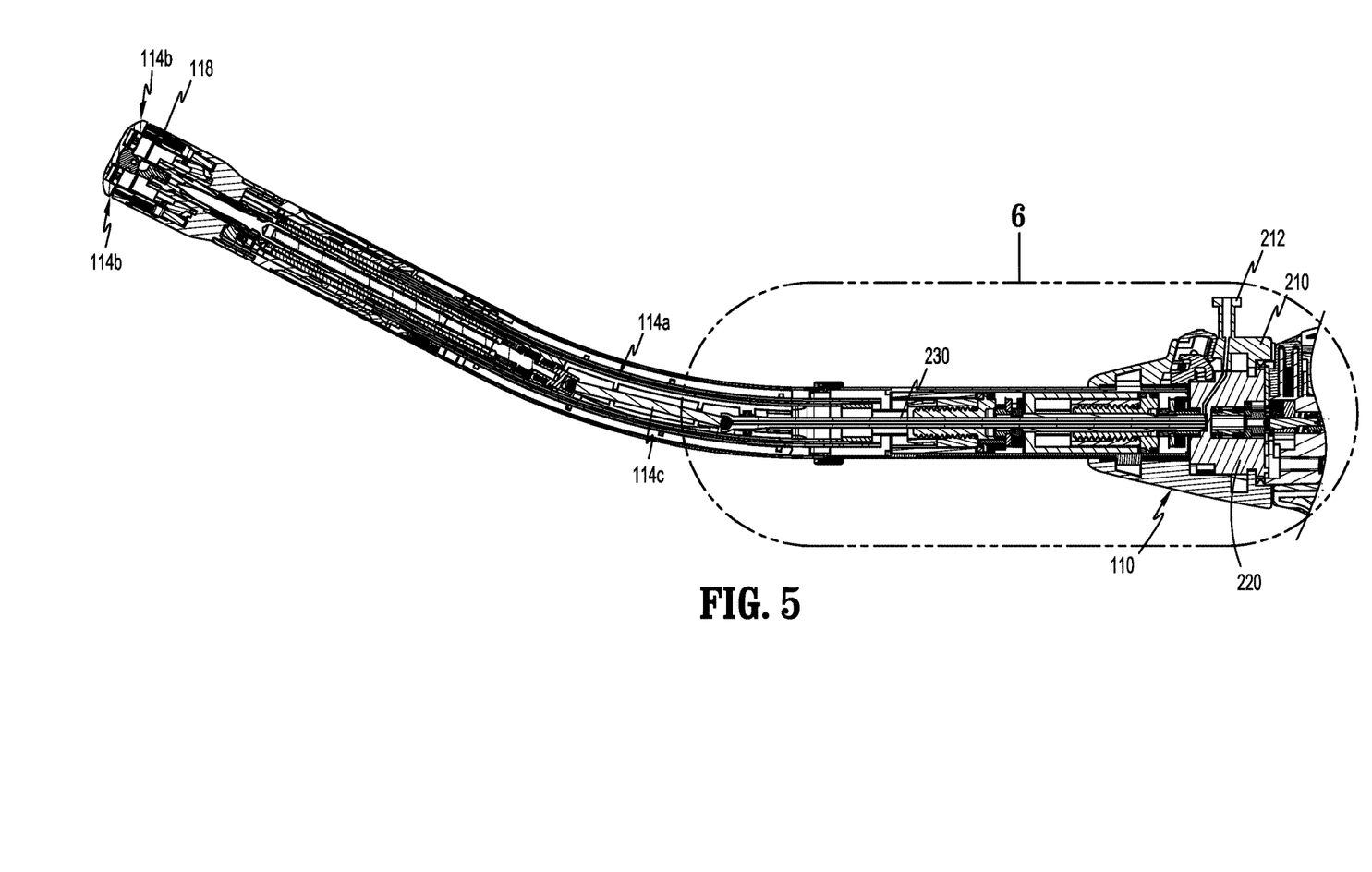
FIG. 5 is a cross-sectional view of a distal portion of the surgical system of FIG. 1 as taken along section line 5-5 of FIG. 1.
Figure 6:
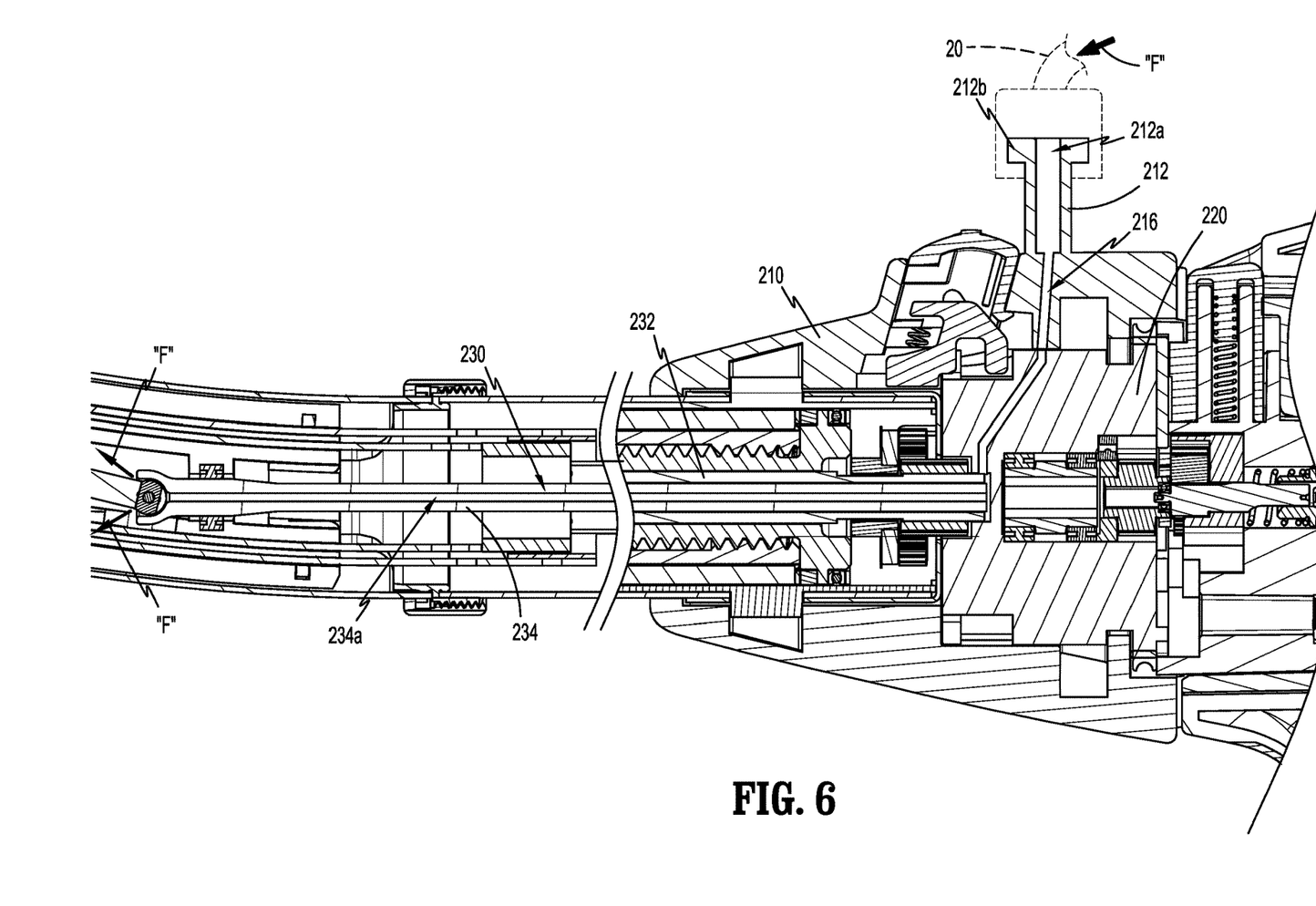
FIG. 6 is an enlarged view of the indicated area of detail shown in FIG. 5 with portions of the surgical system of FIG. 1 shown in phantom for clarity.

In use, fluid conduit 20 is coupled to fluid source 10 at one end and to inlet port 212 at the other end thereof. Fluid "F" is then advanced or pumped via pump 12 from fluid source 10 through fluid conduit 20 into surgical stapling apparatus 110 via inlet port 212 under continuous flow. Fluid "F" then travels through outer housing 210 via passage 212a and first fluid channel 216 and into second fluid channel 224 of inner housing 220. Fluid "F" then advances into third fluid channel 234a for distal release into interior cavity 114c of elongated tubular body portion 114 under positive pressure. The flow of fluid "F" is continuously pushed through irrigation assembly 200 to create a positive pressure gradient and discourage foreign matter such as soil and contaminants from entering the elongated tubular body portion 114 as discussed above. In particular, the interior cavity 114c can be filled with fluid "F" until satiated such that fluid "F" egresses out of surgical instrument 110 through openings thereof such as egress orifices 114b to prevent debris or other contaminants from entering interior cavity 114c. While continuously advancing fluid "F" through surgical stapling apparatus 110, surgical stapling apparatus 110 can be operated, for example, by moving end effector 118 between the open and closed positions thereof and/or by firing end effector 118 to fasten and/or cut tissue clamped between first and second jaw members 120, 122 of end effector 118.

Once the surgical procedure is complete, fluid source 10 can be disconnected from surgical stapling apparatus 110 to stop the continuous flow of fluid "F" therethrough. The fluid "F" can then be drained from surgical stapling apparatus 110 so that any subsequent cleaning techniques (e.g., autoclaving) can be effectuated on any reusable portions of surgical stapling apparatus 110 for subsequent procedures or reuse.

Figure 7:
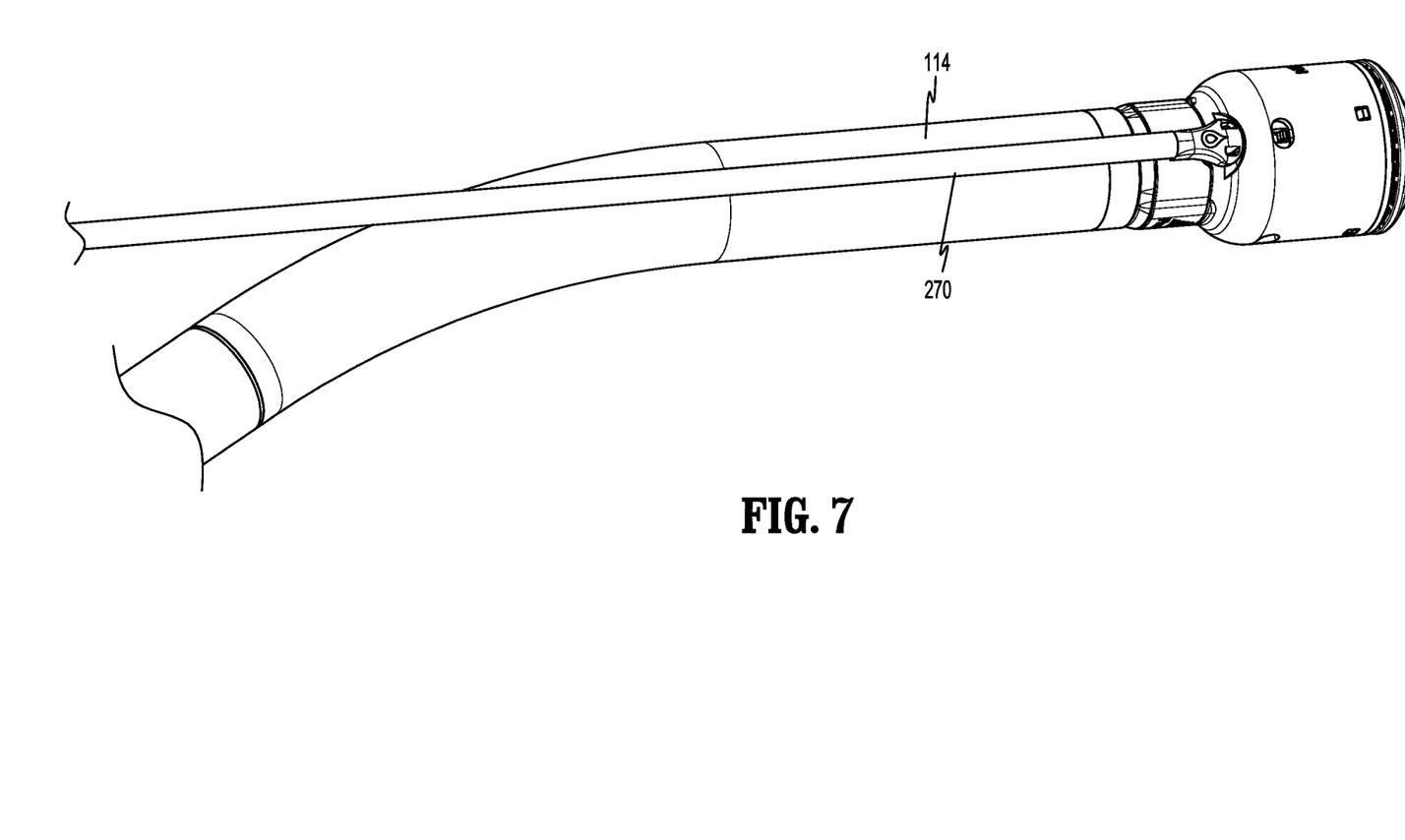
FIG. 7 is an enlarged, side perspective view of a distal portion of the surgical system of FIG. 1 with a return line shown coupled thereto.

As seen in FIG. 7, a relief conduit 240 can be coupled to elongated tubular body portion 114 such as at end effector 118 (e.g., along outer surface thereof) to facilitate removal of excess fluid "F" from surgical stapling apparatus 110. Relief conduit 240 can extend along an outer surface of elongated tubular body portion 114 or within interior cavity 114c of elongated tubular body portion 114. Relief conduit 240 can be coupled to a disposal source (not shown) for disposing of the excess fluid "F" and/or returning the excess fluid "F" back to fluid source "F" for reuse.

In aspects, although fluid "F" is described as entering interior cavity 114c through third fluid channel 234a of shaft assembly 230, the third fluid channel 234a, or any number of third fluid channels can be provided anywhere in interior cavity 114c (e.g., as alternative fluid paths), in addition to, or instead of, being defined through shaft assembly 230.

As can be appreciated, securement of any of the components of the presently disclosed apparatus can be effectuated using known securement techniques such welding, crimping, gluing, fastening, etc.

The various aspects disclosed herein may also be configured to work with robotic surgical systems and what is commonly referred to as "Telesurgery." Such systems employ various robotic elements to assist the clinician and allow remote operation (or partial remote operation) of surgical instrumentation. Various robotic arms, gears, cams, pulleys, electric and mechanical motors, etc. may be employed for this purpose and may be designed with a robotic surgical system to assist the clinician during the course of an operation or treatment. Such robotic systems may include remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of clinicians may prep the patient for surgery and configure the robotic surgical system with one or more of the instruments disclosed herein while another clinician (or group of clinicians) remotely controls the instruments via the robotic surgical system. As can be appreciated, a highly skilled clinician may perform multiple operations in multiple locations without leaving his/her remote console which can be both economically advantageous and a benefit to the patient or a series of patients. For a detailed description of exemplary medical work stations and/or components thereof, reference may be made to U.S. Pat. No. 8,828,023, and PCT Application Publication No. WO2016/025132, the entire contents of each of which are incorporated by reference herein.

Persons skilled in the art will understand that the structures and methods specifically described herein and illustrated in the accompanying figures are non-limiting exemplary aspects, and that the description, disclosure, and figures should be construed merely as exemplary of particular aspects. It is to be understood, therefore, that the present disclosure is not limited to the precise aspects described, and that various other changes and modifications may be effected by one skilled in the art without departing from the scope or spirit of the disclosure. Additionally, it is envisioned that the elements and features illustrated or described in connection with one exemplary aspect may be combined with the elements and features of another without departing from the scope of the present disclosure, and that such modifications and variations are also intended to be included within the scope of the present disclosure. Indeed, any combination of any of the presently disclosed elements and features is within the scope of the present disclosure. Accordingly, the subject matter of the present disclosure is not to be limited by what has been particularly shown and described.

What is claimed is:

1. A surgical instrument, comprising:
    an elongated tubular body portion defining an interior cavity; and
    an irrigation assembly including an inlet port and a shaft assembly supported within the elongated tubular body portion, the inlet port and the shaft assembly in fluid communication with one another to deliver fluid from the inlet port into the interior cavity of the elongated tubular body portion to irrigate the interior cavity with positive fluid pressure.

2. The surgical instrument of claim 1, wherein the elongated tubular body portion includes at least one egress orifice that is configured to enable fluid to exit from the elongated tubular body portion.

3. The surgical instrument of claim 1, wherein the shaft assembly includes an inner shaft and an outer shaft, the inner shaft supported within the outer shaft.

4. The surgical instrument of claim 1, wherein the elongated tubular body portion is configured to removably couple to a handle assembly that operates the end effector, the elongated tubular body portion supporting a housing assembly on a proximal end portion of elongated tubular body portion, wherein a proximal end portion of the housing assembly couples to a distal end portion of the handle assembly to removably couple the elongated tubular body portion to the handle assembly.

5. The surgical instrument of claim 4, wherein the housing assembly includes an outer housing and an inner housing, the outer housing independent of the inner housing and supporting the inlet port.

6. The surgical instrument of claim 5, wherein the inner housing supports a proximal end portion of the shaft assembly.

7. The surgical instrument of claim 6, wherein the outer housing defines a first fluid channel therethrough that is in fluid communication with the inlet port.

8. The surgical instrument of claim 7, wherein the inner housing defines a second fluid channel therethrough that is in fluid communication with the first fluid channel.

9. The surgical instrument of claim 8, wherein the second fluid channel is disposed in fluid communication with a third fluid channel defined within the shaft assembly.

10. The surgical instrument of claim 1, further comprising a relief conduit coupled to the end effector and positioned to remove excess fluid delivered to the elongated tubular body portion.

11. A surgical instrument system, comprising:
    a fluid source;
    an elongated tubular body portion defining an interior cavity; and
    an irrigation assembly coupled to the elongated tubular body portion, the irrigation assembly including an inlet port and a shaft assembly supported by the elongated tubular body portion, the inlet port and the shaft assembly in fluid communication with one another to deliver fluid from the fluid source and into the interior cavity of the elongated tubular body portion via the inlet port to irrigate the interior cavity with positive fluid pressure.

12. The surgical instrument system of claim 11, wherein the elongated tubular body portion includes at least one egress orifice that is configured to enable fluid to exit from the elongated tubular body portion.

13. The surgical instrument system of claim 11, wherein the shaft assembly includes an inner shaft and an outer shaft, the inner shaft supported within the outer shaft.

14. The surgical instrument system of claim 13, wherein the inlet port and the shaft assembly are in fluid communication via at least one fluid channel extending between the inlet port and the shaft assembly.

15. The surgical instrument system of claim 14, wherein the inner shaft is disposed in fluid communication with the at least one fluid channel.

16. The surgical instrument system of claim 1, further comprising a relief conduit coupled to the elongated tubular body portion and positioned to return excess fluid delivered to the elongated tubular body portion back to the fluid source.

17. A surgical stapling system, comprising:
    a fluid source;
    a surgical stapling instrument including an elongated tubular body portion defining an interior cavity; and
    an irrigation assembly in fluid communication with the fluid source and coupled to the elongated tubular body portion, the irrigation assembly including an inlet port in fluid communication with the interior cavity of the elongated tubular body portion to deliver fluid into the interior cavity and irrigate the interior cavity with positive fluid pressure.

18. The surgical stapling system of claim 17, wherein the elongated tubular body portion includes at least one egress orifice that is configured to enable fluid to exit from the elongated tubular body portion.

19. The surgical stapling system of claim 18, further comprising a shaft assembly including an inner shaft and an outer shaft, the inner shaft supported within the outer shaft, wherein the inlet port and the inner shaft are in fluid communication via at least one fluid channel extending between the inlet port and the inner shaft.

20. The surgical stapling system of claim 17, further comprising a relief conduit coupled to the elongated tubular body portion and positioned to enable excess fluid within the elongated tubular body portion to exit from the elongated tubular body portion.

* * * * *